(12) United States Patent
Dorsey

(10) Patent No.: US 8,052,656 B2
(45) Date of Patent: Nov. 8, 2011

(54) ENTERAL FEEDING SYSTEM

(75) Inventor: Michael C. Dorsey, Edwardsville, IL (US)

(73) Assignee: Tyco Healthcare Group LP, Mansfield, MA (US)

( * ) Notice: Subject to any disclaimer, the term of this patent is extended or adjusted under 35 U.S.C. 154(b) by 90 days.

(21) Appl. No.: 12/368,526

(22) Filed: Feb. 10, 2009

(65) Prior Publication Data
US 2010/0204645 A1     Aug. 12, 2010

(51) Int. Cl.
*A61M 5/142*  (2006.01)

(52) U.S. Cl. ........................................ 604/248; 604/246

(58) Field of Classification Search .................. 604/131, 604/151, 236, 244–249, 256; 137/601.11, 137/601.16, 601.17, 867, 876, 877, 616.7; 251/56, 59, 96, 160, 180, 188, 192, 207, 251/208, 283, 286, 292, 304, 345, 352
See application file for complete search history.

(56) References Cited

U.S. PATENT DOCUMENTS

| | | | |
|---|---|---|---|
| 297,794 A | 4/1884 | William | |
| 2,032,723 A | 3/1936 | Schweser | |
| 2,644,450 A | 7/1953 | Krewson | |
| 4,253,501 A | 3/1981 | Ogle | |
| 4,904,245 A * | 2/1990 | Chen et al. | 604/248 |
| 5,002,528 A | 3/1991 | Palestrant | |
| 5,005,604 A * | 4/1991 | Aslanian | 137/556 |
| 5,318,539 A | 6/1994 | O'Neil | |
| 5,356,375 A | 10/1994 | Higley | |
| 5,439,452 A | 8/1995 | McCarty | |
| 5,466,228 A | 11/1995 | Evans | |
| 5,807,312 A | 9/1998 | Dzwonkiewicz | |
| 5,876,378 A | 3/1999 | Mbadugha | |
| 5,911,708 A | 6/1999 | Teirstein | |
| 6,059,747 A | 5/2000 | Bruggeman | |
| 6,656,157 B1 | 12/2003 | Duchon et al. | |
| 6,843,780 B2 | 1/2005 | Larrain | |
| 6,953,450 B2 | 10/2005 | Baldwin | |
| 6,981,967 B2 | 1/2006 | Massengale et al. | |
| 7,092,797 B2 * | 8/2006 | Gaines et al. | 700/282 |
| 7,128,727 B2 * | 10/2006 | Flaherty et al. | 604/131 |
| 2005/0267417 A1 * | 12/2005 | Secrest et al. | 604/247 |
| 2007/0118078 A1 | 5/2007 | McNally et al. | |
| 2008/0223483 A1 * | 9/2008 | Han et al. | 141/198 |

FOREIGN PATENT DOCUMENTS

GB       1297794       11/1972

* cited by examiner

*Primary Examiner* — Nicholas D Lucchesi
*Assistant Examiner* — Quynh-Nhu H Vu
(74) *Attorney, Agent, or Firm* — Elias Domingo

(57) ABSTRACT

A valve mechanism for use with a feeding set includes a reservoir of liquid and a metering device. The valve mechanism includes a valve body including a reservoir port adapted to be fluidly connected to the reservoir, a metering port adapted to be fluidly connected to the metering device, a feeding port adapted to be in fluid communication with the patient, and a priming port in fluid communication with atmosphere. A valve member in the valve body is adapted to selectively fluidly connect the reservoir port to the priming port, to fluidly connect the reservoir port to the metering port, and to fluidly connect the metering port to the feeding port.

11 Claims, 4 Drawing Sheets

ENTERAL FEEDING SYSTEM

FIELD OF THE INVENTION

The present invention generally relates to an enteral feeding system, and more generally, to a valve for use with the feeding system.

BACKGROUND OF THE INVENTION

There are different ways of enterally administrating liquid nutrient and/or liquid medicine to a patient. One way of enteral feeding is by gravity. A feeding tube, such as a nasogastric feeding tube, running from a container of liquid nutrients and/or medicine is inserted into the stomach of the patient, and the liquid flows, by gravity, into the stomach of the patient. Gravity feeding delivers a large amount of liquid in a short period of time. Another way of enterally feeding is by using a peristaltic pump that delivers the liquid to the patient at a controlled rate of delivery. Peristaltic feeding pumps are well known in the art.

Enterally feeding adults and children by either gravity feeding or using peristaltic pump is typically satisfactory. However, these types of feeding are typically not satisfactory for enterally feeding neonates, such as neonates born prematurely, who may require a feeding rate of 1 mL per hour, or even as low as 0.1 mL per hour. Gravity feeding is not satisfactory typically because the liquid is delivered much too quickly in an uncontrolled manner. Moreover, feeding by a peristaltic pump is not satisfactory typically because the peristaltic pumps also delivery the liquid too quickly and are not precise enough to accurately deliver the small amounts of liquid necessary for neonatal use.

Because of the unsatisfactory results of feeding neonates by gravity and using a peristaltic pump, syringe pumps are currently used for neonatal enteral feeding. Syringe pumps are typically precise and have low flow rates. A common syringe pump suitable for neonatal enteral feeding includes a syringe loaded on a pump device. The pump device includes a piston that engages a plunger of the syringe. The piston is aligned with the plunger and moves linearly to depress the plunger and expel the liquid out the syringe to deliver the liquid to the patient. Typically, the liquid, such as breast milk, may be in a container and an amount of the liquid is loaded into the syringe manually before the syringe is loaded onto the pump device.

SUMMARY OF THE INVENTION

In one aspect, a valve mechanism for use with a feeding set including a reservoir of liquid and a metering device generally comprises a valve body including a reservoir port adapted to be fluidly connected to the reservoir. A metering port is adapted to be fluidly connected to the metering device. A feeding port is adapted to be in fluid communication with the patient and a priming port in fluid communication with atmosphere. A valve member in the valve body is adapted to selectively fluidly connect the reservoir port to the priming port, to fluidly connect the reservoir port to the metering port, and to fluidly connect the metering port to the feeding port.

In another aspect, an enteral feeding set generally comprises a valve mechanism including a reservoir port, a syringe port, a feeding port, and a priming port in fluid communication with atmosphere. A reservoir is fluidly connected to the reservoir port of the valve mechanism. The reservoir is adapted for holding a quantity of liquid. A syringe is fluidly connected to the syringe port of the valve mechanism for aspirating a quantity of liquid from the reservoir and delivering the quantity of liquid to a patient. The valve mechanism is operable in a priming configuration to fluidly connect the reservoir to the priming port to prime the valve mechanism. The valve mechanism is operable in a metering configuration to fluidly connect the reservoir to the syringe and to block fluid communication between the reservoir and the priming port, thereby allowing a quantity of liquid to be metered from the reservoir by operating the syringe. The valve mechanism is operable in a feeding configuration to fluidly connect the syringe to the feeding port and to block fluid communication between the reservoir and the syringe, thereby allowing liquid to be delivered to the patient by operating the syringe.

In yet another aspect, an enteral feeding system generally comprises a valve mechanism having a reservoir port, a priming port, a metering port and a feeding port. The valve mechanism is configurable between a priming configuration in which the reservoir port and the priming port are fluidly connected, a metering configuration in which the reservoir port and the metering port are fluidly connected, and a feeding configuration in which the metering port and the feeding port are fluidly connected. A power-driven valve actuator is operatively connected to the valve mechanism for configuring the valve mechanism between said priming configuration and said metering configuration. A reservoir for holding a quantity of liquid is in fluid communication with the reservoir port of the valve mechanism. A syringe is in fluid communication with the metering port. A priming sensor is disposed to detect liquid in the reservoir port of the valve mechanism. A controller is in communication with the priming sensor and the valve actuator. The priming sensor is adapted to send a signal to the controller indicative of the system being primed when the sensor detects liquid. In response to receiving the signal from the priming sensor, the controller is adapted to activate the valve actuator to configure the valve mechanism in the metering configuration.

In another aspect, a method of feeding a nutritional liquid to a patient using an automated feeding device generally comprises connecting a reservoir of nutritional liquid to a valve mechanism through a first tubing. The reservoir and the first tubing are placed in fluid communication with a priming port of the valve mechanism so that nutritional liquid in the reservoir flows to the valve mechanism through the first tubing, thereby priming the first tubing and removing air from the reservoir tubing. A first quantity of nutritional liquid is aspirated from the reservoir and the first tubing through the valve mechanism and into a syringe of the automated feeding device. The first quantity of liquid is dispensed from the syringe through the valve mechanism to the patient. A second quantity of nutritional liquid is aspirated from the reservoir and the first tubing through the valve mechanism and into the syringe without re-priming the first tubing, whereby feeding from the syringe to the patient can be carried out semi-continuously.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
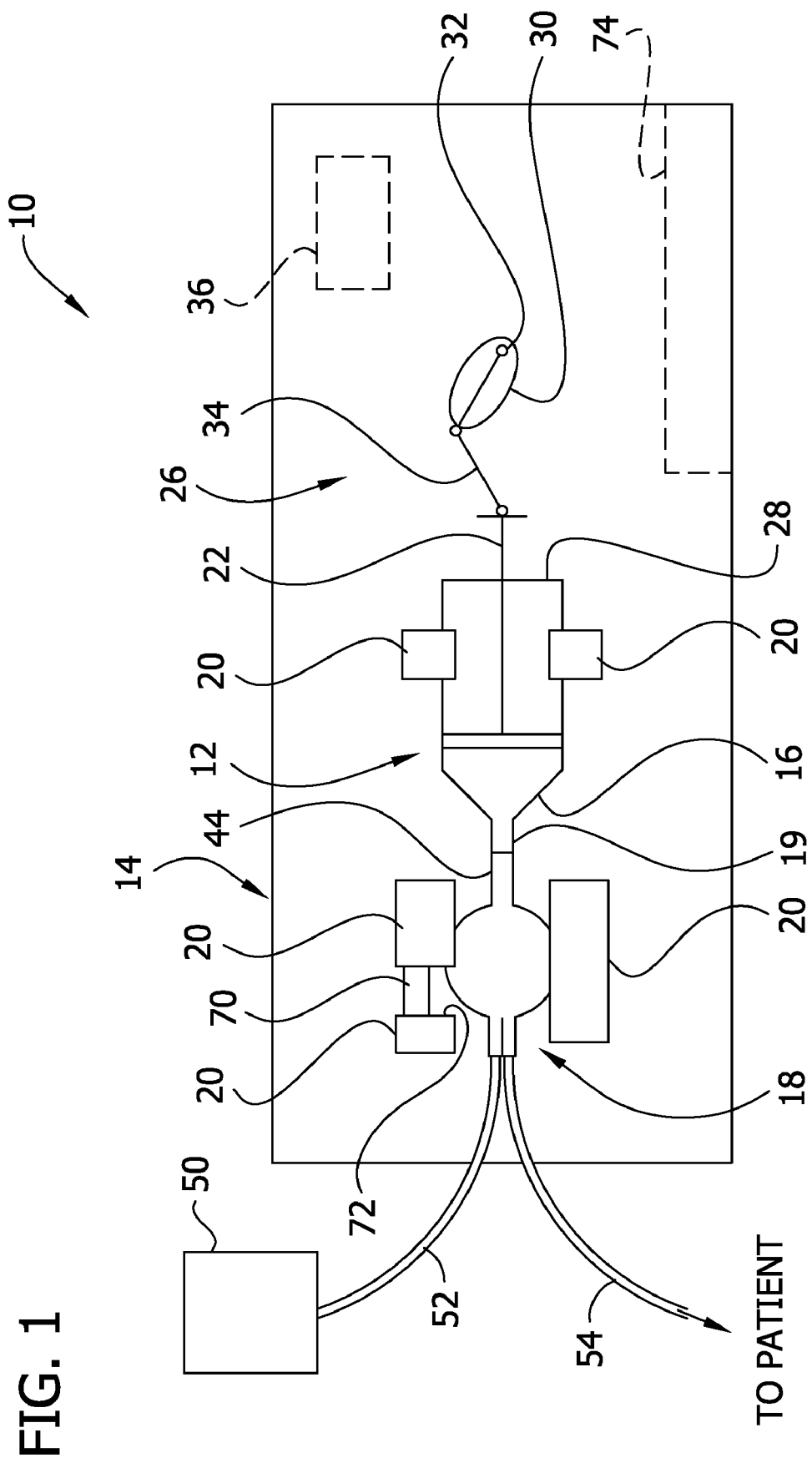
FIG. 1 is a schematic of an enteral feeding system illustrating a feeding set mounted on an automated feeding device.
Figure 2:
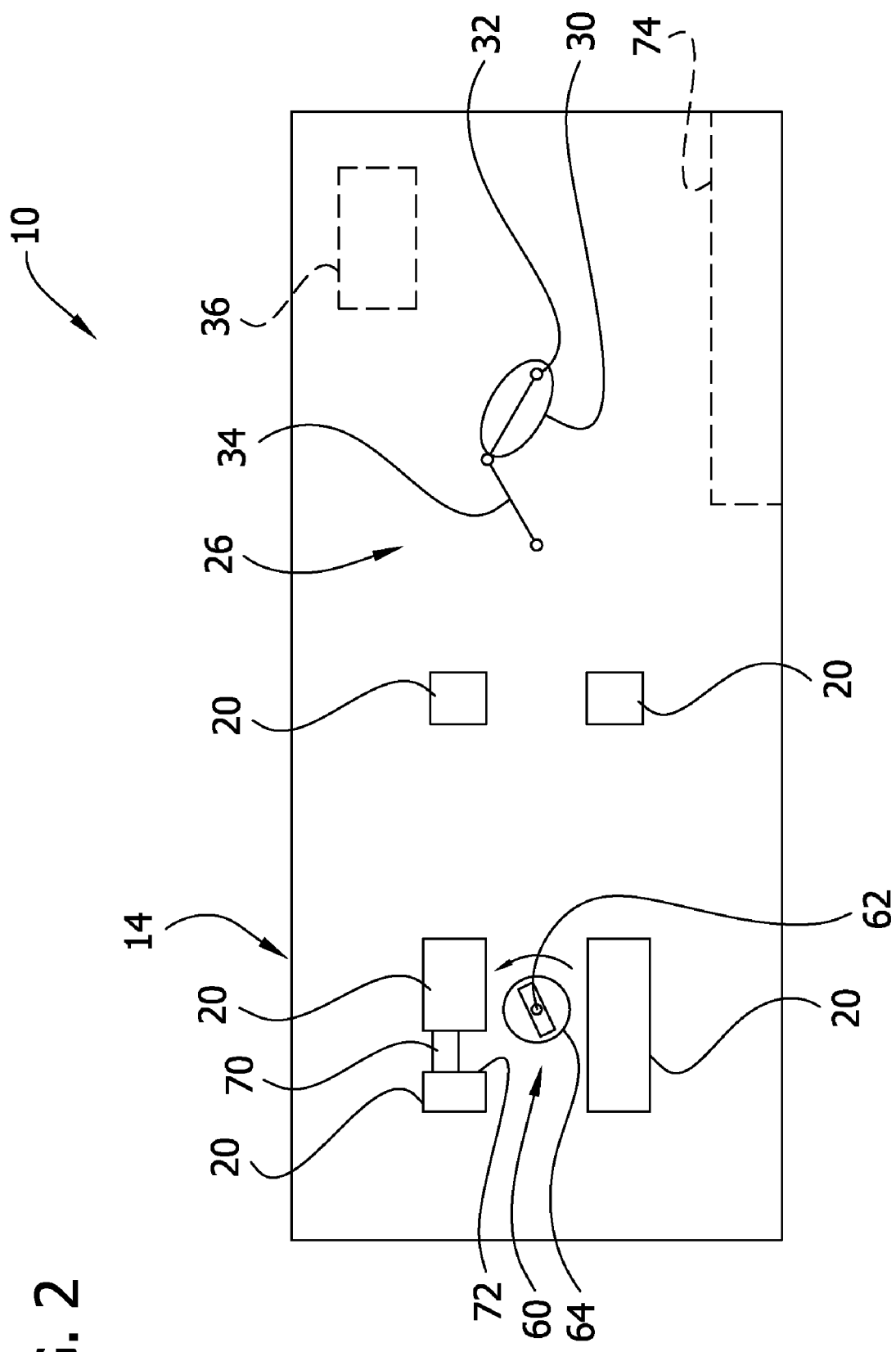
FIG. 2 is a schematic of the automated feeding device of the enteral feeding system.

Referring now to the drawings, an embodiment of an enteral feeding system for enterally feeding a patient, such as a neonate, is generally indicated at 10. In general, the feeding system comprises a feeding set, generally indicated at 12, and an automated feeding device, generally indicated at 14, on which the feeding set is mounted. Overall, the feeding system 10 is configured to allow for liquid nutrients such as breast milk and/or medicine to be automatically delivered to the patient as either continuous feeding or bolus feeding.

Referring to FIG. 1, the feeding set 12 includes a syringe 16 (broadly, a metering device) and a valve mechanism 18 secured the syringe in communication with an outlet 19 of the syringe. The valve mechanism 18 and the syringe 16 are removably secured to mounts 20 on the automated feeding device 14. The mounts 20 define slots (not shown), and the valve mechanism 18 and the syringe 16 are slid into these slots to secure the valve mechanism and the syringe to the automated feeding device 14. The automated feeding device 14 may include stops (not shown) or catches (not shown) or other components that releasably engage the valve mechanism 18 and/or the syringe 16 to hold the valve mechanism and the syringe in place relative to the mounts 20. The valve mechanism 18 and the syringe 16 may be withdrawn from the slots to remove the valve mechanism and the syringe from the automated feeding device 14. Other ways of securing the valve mechanism 18 and the syringe 16 to the automated feeding device 14 do not depart from the scope of the present invention.

A plunger 22 of the syringe 16 is operatively connected to a crank-slider mechanism, generally indicated at 26, of the automated feeding device 14 to produce reciprocating back and forth movement of the plunger in a barrel 28 of the syringe, as explained in more detail below. The mechanism 26 comprises a crank 30 operatively connected to a drive shaft 32 of motor, such as an electric motor (not shown), inside the automated feeding device 14 to produce rotational movement of the crank. Opposite ends of a connecting rod or linkage 34 are operatively, i.e., pivotally, connected to the crank 30 and the plunger 22 to convert rotational motion of the crank into translational motion of the plunger in the barrel 28. The connecting rod 34 is releasably secured to the plunger 22 so that the syringe 16 may be removed from the automated feeding device 14. For example, the connecting rod 34 and the plunger 22 may include mateable snap-fit connectors that form a hinge. Others connections do not depart from the scope of the present invention. As will be explained below, operation of the crank-slider mechanism, and more specifically the motor of the crank-slider mechanism, is controlled by a controller 36 located inside the automated feeding device. Other mechanical and/or automated ways of reciprocating the plunger 22 do not depart from the scope of the present invention. Moreover, it is understood that the feeding set 12 may be used apart from the automated feeding device 14, and that the plunger 22 may be moved manually, with or without the aid of a mechanical device.

Referring to FIGS. 1 and 3-6, the valve mechanism 18 of the illustrated embodiment includes a valve body 38 defining a reservoir port 40, a feeding port 42, a syringe port 44 and a priming port 46. The reservoir port 40 is fluidly connected to a liquid reservoir or container 50 via first tubing 52, although the reservoir port and the reservoir may be fluidly connected in other ways. The feeding port 42 is fluidly connected to the patient via second tubing 54, although the feeding port and the patient may be fluidly connected in other ways. The syringe port 44 is fluidly connected to the outlet 19 of the syringe 16 via a suitable connection, such as a luer-type connection or other connections. Alternatively, the valve mechanism 18 and the syringe 12 may be integrally formed or connected by tubing or in other ways. Finally, the priming port 46 is in fluid communication with the atmosphere.

A valve member 58 is rotatable inside the valve body 38 so that selected ports 40, 42, 44, 46 are in fluid communication via a passage 59 in the valve member. In the illustrated embodiment, the valve member 58 is a hollow member having an outer wall with a pair of openings 59a, 59b communicating with an interior cavity 59c of the valve member to define the flow passage 59. The two openings 59a, 59b are configured such that the valve member is rotatable to different positions to provide different valve configurations, including a closed configuration (not shown) in which flow through the valve member is blocked, a priming configuration (FIG. 3), a metering configuration (FIG. 4), and a feeding configuration (FIG. 5). It will be understood that the valve member 58 could be configured to have multiple separate passages arranged such that rotation of the valve member to different positions aligns particular passages with corresponding ports to provide the desired valve configurations (i.e., flow paths). The valve mechanism 18 of the illustrated embodiment is similar to the valve mechanism disclosed in U.S. application Ser. No. 10/853,958, filed May 25, 2004, the entirety of which is herein incorporated by reference.

The valve member 58 is operatively connected to a valve actuator 60 of the automated feeding device 14. In the illustrated embodiment, the valve actuator 60 comprises an output shaft 62 of a motor (not shown) in the automated feeding device 14. A key 64 at the free end of the output shaft 62 is sized and shaped for sliding reception in a slot 66 (FIG. 6) defined by the valve member 58 when the valve mechanism 18 is secured to the automated feeding device. As will be explained below, the actuator 60 rotates the valve member 58 to configure the valve mechanism 18 between the various valve configurations explained above. Operation of the actuator 60 is controlled by the controller 36 located inside the automated feeding device 14. Other mechanical and/or automated ways of rotating the valve member 58 do not depart from the scope of the present invention. Moreover, it is understood that the feeding set 12 may be used apart from the automated feeding device 14, and the valve member 58 may be rotated manually, with or without the aid of a mechanical device.

In one embodiment, the automated feeding device 14 includes a priming sensor 70, in communication with the controller 36, for detecting when liquid from the liquid reservoir 50 has completely filled the first tubing 52 and/or the valve member 58. In the illustrated embodiment, the priming sensor 70 includes an optical sensor that detects when liquid is present in the priming port 46 and sends a signal indicating the same to the controller 36. The optical sensor 70 is received in an opening or cavity 72 in the mount 20 that secures the valve mechanism 18 to the automated feeding device 14 so that the sensor is proximate to the priming port 45. The priming sensor 70 may be positioned at other locations on the automated feeding device 14 to detect when liquid is present in the valve member 58 and/or the reservoir port 40 without departing from the scope of the present invention. Moreover, sensors other than optical sensors may be used to detect the presence of liquid in the reservoir port 40 and/or the valve member 58.

In an exemplary use, the feeding set 12 is first mounted on the automated feeding device 14. The valve mechanism 18 is slid into respective mounts 20 so that the key 64 on the output shaft 62 is received in the slot 66 of the valve disc 58, and the syringe 16 is also slid into respective mounts. The connecting rod 34 is connected to the plunger 22. The first tubing 52 is connected to the reservoir 50 and the reservoir port 40. The reservoir 50 is positioned above the reservoir port 40 and may be secured to a stand or an upper surface of the automated feeding device 14. The second tubing 54 is connected to the feeding port 42 and inserted into the patient for enteral feeding. Initially, the valve mechanism 18 is configured in the closed configuration so that each of the ports 40, 42, 44, 46 is closed.

With the feeding set 12 mounted on the automated feeding device 14, a user selects a feeding protocol of the controller 36 using a user interface 74 of the automated feeding device 14. The controller 36 may be programmed with numerous and various feeding protocols. Two such protocols may be continuous feeding and bolus feeding. In general, a continuous feeding protocol involves delivering a selected amount of liquid nutrients from the reservoir 50 to the patient continuously over a selected period of time. On the other hand, a bolus feeding protocol generally involves delivering a selected amount of liquid nutrients from the reservoir to the patient in a single dose, or effectively, all at once. The controller 36 may be programmed to receive selected parameters from the user interface, including an amount to be delivered and a time period for delivering the liquid. The controller 36 may be programmed in other ways without departing from the scope of the present invention.

Figure 3:
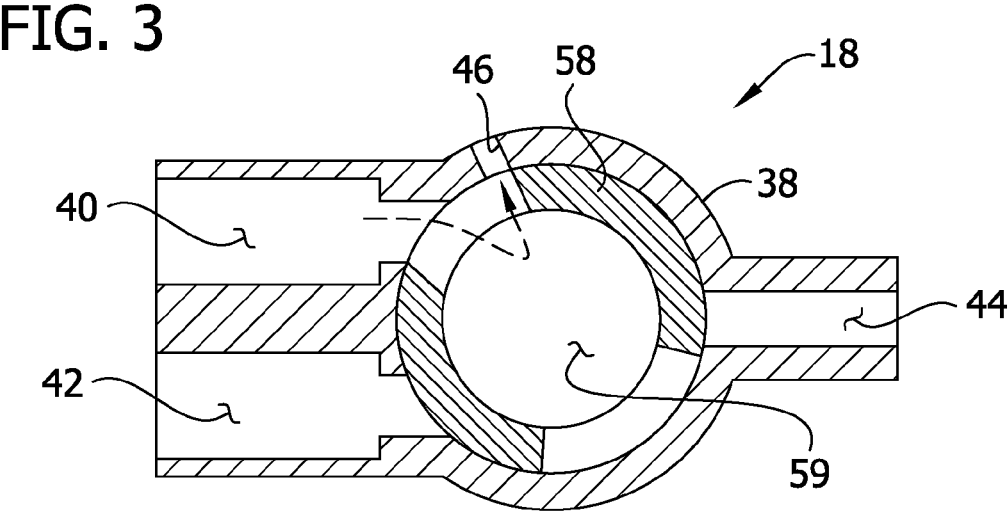
FIG. 3 is a section of a valve mechanism of the syringe feeding set in a priming configuration.

After the protocol has been selected and any necessary parameters have been input to the controller 36, the feeding set 12 is primed. The controller activates the valve actuator motor to turn the actuator 60 and in turn to rotate the valve disc 58 so that the valve mechanism 18 is in its priming configuration (FIG. 3). In this configuration, the reservoir port 40 is fluidly connected to the priming port 46 via the passage 59 in the valve member, and the feeding port 42 and the syringe port 44 are closed. With the reservoir port 40 fluidly connected to the priming port 46 and atmosphere, liquid from the reservoir flows, by gravity, through the first tubing 52 toward the reservoir port and the valve member 58. The sensor 70 detects the liquid flowing into the valve member 58 and sends a signal to the controller 36 indicating that the valve mechanism 18 is primed.

Figure 4:
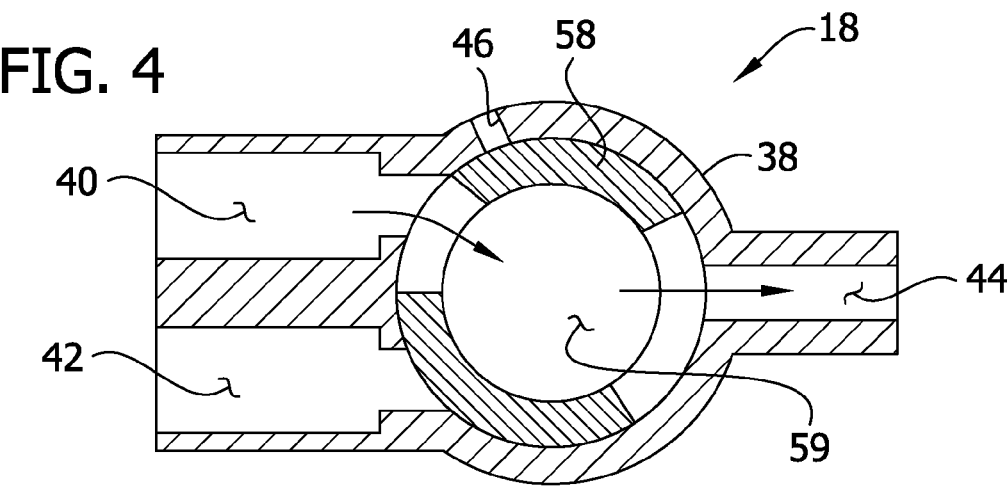
FIG. 4 is a section of the valve mechanism in a metering configuration.
Figure 5:
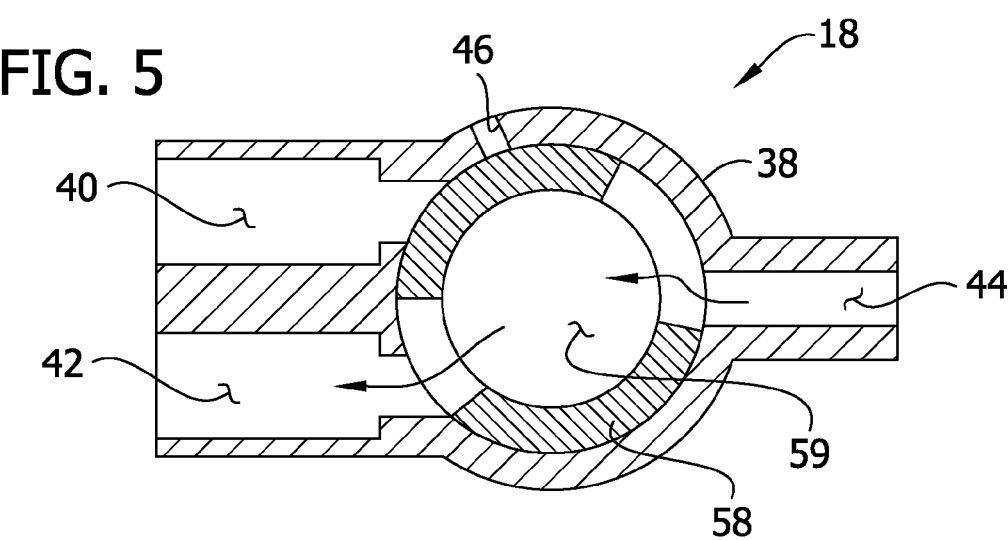
FIG. 5 is a section of the valve mechanism in a delivering configuration.
Figure 6:
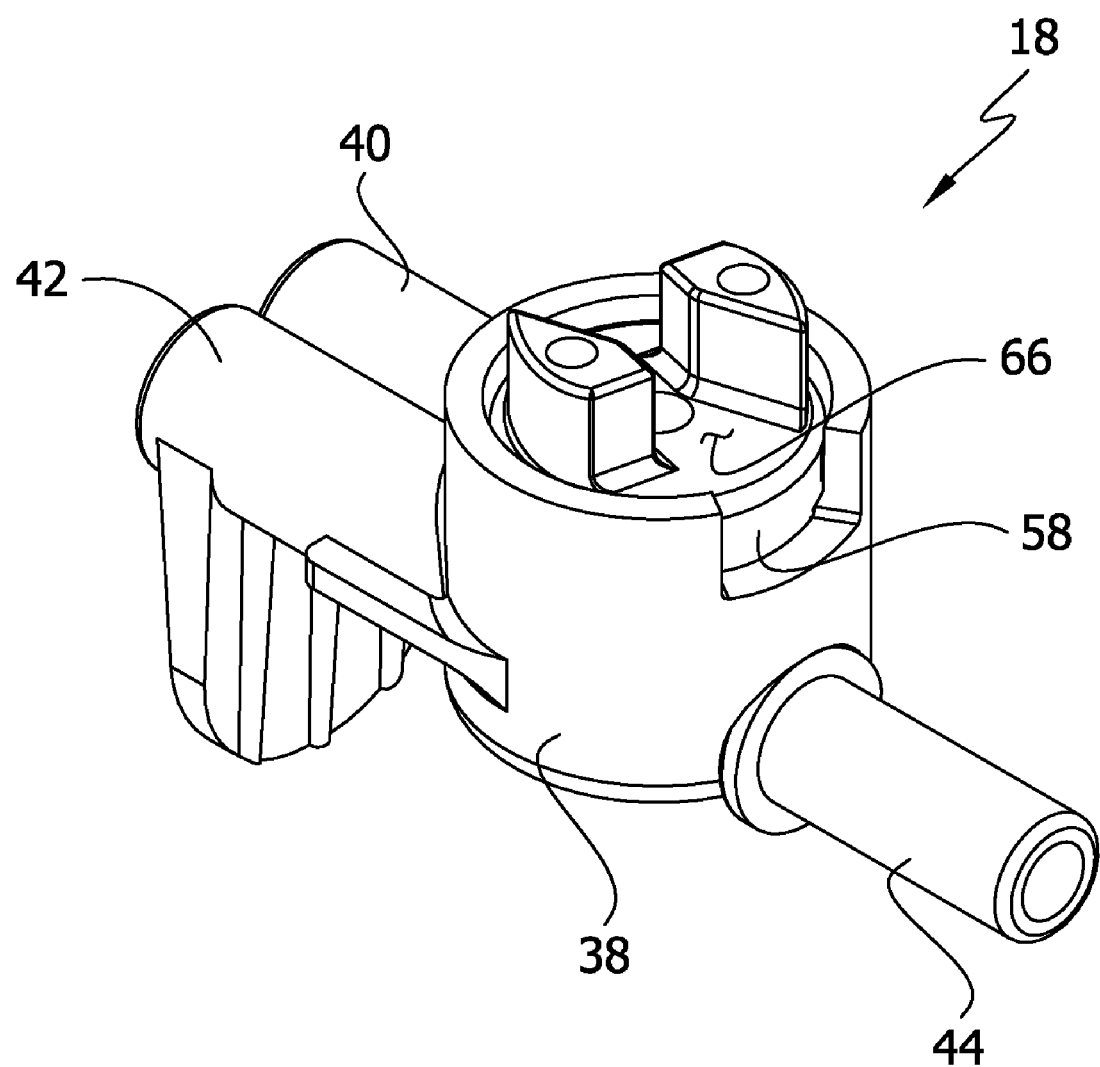
FIG. 6 is rear perspective of the valve mechanism.

When the controller 36 receives the signal that the valve mechanism 18 is primed, the controller activates the valve actuator motor to turn the actuator 60, and, in turn, to rotate the valve member 58 so that the valve mechanism assumes its metering configuration (FIG. 4). In the metering configuration, the reservoir port 40 is fluidly connected to the syringe port 44 via the passage 59. Initially, the plunger 22 is fully depressed in the barrel 28 (i.e., toward the outlet 19). With the valve mechanism 18 in the metering configuration, the controller 36 activates the crank-slider motor (not shown) to rotate the crank 30 in a first direction (e.g., clockwise) and retract the plunger 22 in the barrel 28. As the plunger 28 retracts, liquid is aspirated through the barrel port 44 and into the barrel 28 of the syringe. In one example, the amount of liquid aspirated into the barrel, as determined by the operation of the crank-slider 26, is dependent on the protocol selected by the user and/or parameters inputted to the controller 36. In a first feeding example, if the protocol and/or input parameters calls for an amount of liquid that is less than the maximum quantity deliverable by the syringe 16 in a single discharge, then the controller 36 turns the crank 30 until the barrel 28 fills with a substantially precise, selected quantity of liquid from the reservoir, and then the controller stops the crank. In a second feeding example, the controller 36 continues to turn the crank 30 in the first direction (e.g., clockwise), until the maximum quantity of liquid is aspirated into the barrel 28, as explained in more detail below.

With the desired quantity of liquid in the barrel 28, the controller 36 activates the actuator motor (not shown) to rotate the valve member 58 so that the valve mechanism 18 is in the feeding configuration (FIG. 4). In this configuration, the syringe port 44 is fluidly connected to the feeding port 42 via the passage 59 in the valve member 58. In the first feeding example above, the controller 36 then turns the crank 30 in an opposite second direction (e.g., counter-clockwise) to depress the plunger 22 so that the selected quantity of liquid in the syringe is delivered to the patient. The speed at which the crank 30 is turned, and in effect the speed at which the plunger is depressed, depends on whether the bolus or continuous feeding protocol was selected and the parameters (e.g., amount over time) that were input. In the second feeding example above, the controller 36 continues to turn the crank in the same first direction after the valve mechanism 18 is in the feeding configuration. The configuration and arrangement of the crank-slider 26 is such that rotating the crank 30 an initial portion of a complete revolution (e.g., 180 degrees) retracts the plunger 22 and continuing to rotate the crank a remainder portion of the complete revolution (e.g., remaining 180 degrees) depresses the plunger. The speed at which the crank 30 is turned as the plunger 22 depresses, and in effect the speed at which the plunger is depressed, depends on whether the bolus or continuous feeding protocol was selected and the parameters (e.g., amount over time) that were input.

In addition, in a third feeding example, if the protocol and/or input parameters calls for an amount of liquid that is greater than the maximum quantity deliverable by the syringe 16 in a single discharge such as continuous feeding, the controller 36 continuously rotates the crank 30 more than one complete revolution (i.e., more than 360 degrees) and configures the valve mechanism 18 in the necessary configurations throughout rotation of the crank such that immediately after an initial metered portion of liquid is completely discharged from the syringe, the syringe is reloaded with an appropriate amount of liquid and then discharged as the crank continues to rotate. This cycle of continuously reloading and discharging (i.e., continuously feeding) can continue without re-priming the valve mechanism 18 until the appropriate amount of liquid has been delivered to the patient.

As will be understood from above disclosure, the feeding system 10 allows for precise metering and delivery of small amount(s) of liquid nutrient to a patient, such as a neonatal patient. Precise metering and delivery is especially advantageous when feeding a neonatal patient.

Another feature of the illustrated enteral feeding system 10 allows for the feeding set 12 (more generally, the valve mechanism 18, and more generally still the first tubing 52) to be automatically primed at the onset of the feeding to minimize or eliminate loss of liquid. In one example, the priming sensor 70 and the controller 36 act together to ensure that the feeding set 12 is primed while also preventing the liquid from flowing out the priming port 46 because the priming sensor detects the liquid before the liquid flows out the priming port and upon receiving the signal from priming sensor that the valve mechanism 18 is primed, the controller 36 immediately closes the priming port before liquid can escape through the priming port. This automated priming mechanism reduces waste of the liquid, which may be precious breast milk, and ensures that the system is completely primed so that air is not delivered to the patient along with the liquid. The automated priming mechanism also makes the initial set up of the system 10 easier and more time efficient for the operator.

An additional feature is that the crank-slider mechanism 26 of the feeding system 10 allows for semi-continuous feeding, such as when the crank 30 continuously rotates for more than one revolution, without the need to re-prime the system. As discussed above, after initial priming, the valve mechanism 26 only needs to switch (cycle) between the metering configuration and the feeding configuration to continue feeding after the syringe 16 has delivered an initial maximum deliverable quantity. Moreover, the speed of the crank 30 is controllable by the controller to control the rate at which the liquid is feed to the patient. Controlling the rate of feeding allows for both continuous feeding and bolus feeding.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A valve mechanism for use with a feeding set including a reservoir of liquid and a metering device, the valve mechanism comprising:
    a valve body including a reservoir port adapted to be fluidly connected to the reservoir, a metering port adapted to be fluidly connected to the metering device, a feeding port adapted to be in fluid communication with the patient, and a priming port in fluid communication with and opening directly to atmosphere;
    a valve member in the valve body adapted to selectively fluidly connect the reservoir port to the priming port, to fluidly connect the reservoir port to the metering port, and to fluidly connect the metering port to the feeding port; wherein in no configuration is the metering port placeable in fluid connection with the priming port.

2. A valve mechanism as set forth in claim 1 wherein the valve member is movable to configure the valve mechanism between a priming configuration in which the reservoir port is fluidly connected to the priming port, a metering configuration in which the reservoir port is fluidly connected to the metering port and the priming port is no longer in fluid communication with the reservoir port, and a feeding configuration in which the metering port is fluidly connected to the feeding port and the metering port is no longer in fluid communication with the reservoir port.

3. A valve mechanism as set forth in claim 2 wherein the valve member comprises a rotatable valve member in the valve body.

4. A valve mechanism as set forth in claim 2 further comprising a priming sensor for detecting liquid in at least one of the reservoir port, the valve member and the priming port.

5. A valve mechanism as set forth in claim 1 wherein the reservoir port, the feeding port and the metering port each define a respective flow axis in the direction of fluid flow through the port, the flow axes of the reservoir port, feeding port and metering port being parallel to one another.

6. A valve mechanism as set forth in claim 5 wherein the priming port defines a flow axis in the direction of fluid flow through the port, the flow axis of the priming port being skew to the flow axes of the reservoir port, the feeding port and the metering port.

7. An enteral feeding set comprising:
    a valve mechanism including a reservoir port, a metering port, a feeding port, and a priming port in fluid communication with atmosphere;
    a reservoir fluidly connected to the reservoir port of the valve mechanism, said reservoir being adapted for holding a quantity of liquid;
    a syringe fluidly connected to the metering port of the valve mechanism for aspirating a quantity of liquid from the reservoir and delivering the quantity of liquid to a patient;
    wherein the valve mechanism is operable in a priming configuration to fluidly connect the reservoir to the priming port to prime the valve mechanism,
    wherein the valve mechanism is operable in a metering configuration to fluidly connect the reservoir to the metering port and to block fluid communication between the reservoir and the priming port, thereby allowing a quantity of liquid to be metered from the reservoir by operating the syringe, and wherein the valve mechanism is operable in a feeding configuration to fluidly connect the metering port to the feeding port and to block fluid communication between the reservoir and the metering port, thereby allowing liquid to be delivered to the patient by operating the syringe,
    wherein no configuration is the metering port placeable in fluid connection with the priming port.

8. An enteral feeding set as set forth in claim 7 wherein the valve mechanism includes a valve body and a valve member adapted for movement in the valve body, the valve member being movable to configure the valve mechanism between said priming configuration, said metering configuration, and said feeding configuration.

9. An enteral feeding set as set forth in claim 8 wherein the valve member is a cylindrical valve member rotatable in the valve body.

10. An enteral feeding set as set forth in claim 7 further comprising a first tubing fluidly connecting the reservoir to the reservoir port of the valve mechanism, and a priming sensor for detecting when liquid from the reservoir has completely filled the first tubing.

11. An enteral feeding set comprising:
    a valve mechanism including a reservoir port, a metering port, a feeding port, and a priming port in fluid communication with atmosphere;
    a reservoir fluidly connected to the reservoir port of the valve mechanism, said reservoir being adapted for holding a quantity of liquid;
    a syringe fluidly connected to the metering port of the valve mechanism for aspirating a quantity of liquid from the reservoir and delivering the quantity of liquid to a patient; wherein the valve mechanism is operable in a priming configuration to fluidly connect the reservoir to the priming port to prime the valve mechanism, wherein the valve mechanism is operable in a metering configuration to fluidly connect the reservoir to the metering port and to block fluid communication between the reservoir and the priming port, thereby allowing a quantity of liquid to be metered from the reservoir by operating the syringe, and wherein the valve mechanism is operable in a feeding configuration to fluidly connect the metering port to the feeding port and to block fluid communication between the reservoir and the metering port, thereby allowing liquid to be delivered to the patient by operating the syringe, wherein the valve body and the valve mechanism are adapted to prevent fluid communication between the metering port and the priming port; and in combination with a power-driven valve actuator operatively connected to the valve mechanism for configuring the valve mechanism between said priming configuration and said metering configuration;

a priming sensor disposed to detect liquid in the reservoir port of the valve mechanism; and a controller in communication with the priming sensor and the valve actuator, wherein said priming sensor is adapted to send a signal to the controller indicative of the system being primed when the sensor detects liquid, wherein in response to receiving the signal from the priming sensor, said controller activates the valve actuator to configure the valve mechanism in said metering configuration.

* * * * *